United States Patent [19]
Fujita et al.

[11] Patent Number: 5,965,746
[45] Date of Patent: Oct. 12, 1999

[54] EFFICIENT METHOD FOR THE SYNTHESIS OF N-CYCLIC MALEAMIC ACIDS AND N-CYCLIC MALEIMIDES

[75] Inventors: Satoshi Fujita, Nisshin; Paidi Yella Reddy, Nagoya; Takeshi Toru, Aichi-gun, all of Japan

[73] Assignee: Aisin Seiki Kabushiki Kaisha, Kariya, Japan

[21] Appl. No.: 09/089,235

[22] Filed: Jun. 2, 1998

[30] Foreign Application Priority Data

Jun. 2, 1997 [JP] Japan ..................................... 9-160454

[51] Int. Cl.$^6$ ................. C07D 207/325; C07D 207/452; C07D 409/00; C07D 207/40
[52] U.S. Cl. ........................ 548/525; 548/545; 548/547; 548/548; 548/549; 548/550
[58] Field of Search ..................... 548/549, 545, 548/547, 548, 550, 525

[56] References Cited

U.S. PATENT DOCUMENTS

| | | | |
|---|---|---|---|
| 2,444,536 | 7/1948 | Searle ....................................... | 548/549 |
| 3,891,670 | 6/1975 | Kanoka et al. ........................... | 548/549 |
| 4,180,508 | 12/1979 | Becker et al. ........................... | 548/549 |
| 4,213,904 | 7/1980 | Haugland ................................ | 544/212 X |
| 4,217,282 | 8/1980 | Heitmann ................................ | 548/549 |
| 5,079,331 | 1/1992 | Kitahara et al. .......................... | 528/96 |
| 5,475,021 | 12/1995 | Marnet et al. ............................ | 514/425 |
| 5,508,427 | 4/1996 | Tagami et al. ........................... | 548/406 |
| 5,684,163 | 11/1997 | Groth et al. .............................. | 548/549 |
| 5,741,913 | 4/1998 | Oda et al. ................................. | 548/548 |
| 5,773,630 | 6/1998 | Groth et al. .............................. | 548/545 |

OTHER PUBLICATIONS

Mehta et al., "Maleamic and Citraconamic Acids, Methyl Esters, and Imides," *J. Org. Chem.,* (1960) vol. 25, pp. 1012–1015.

Meyers et al., "A Facile Synthesis of Chiral Bicyclic Lactams Utilized in the Formation of Chiral Quaternary Carbon Compounds," *J. Org. Chem.,* (1989), vol. 54, pp. 4243–4246.

Garner et al., "Development of an Asymmetric Approach to the 3,8–Diazabicyclo[3.2.1.]octane Moiety of Quinocarcin via Intermolecular 1,3–Dipolar Cycloadditions of Photochemically Generated Azomethine Ylides," *J. Org. Chem.,* (1991) vol. 56, pp. 5893–5903.

Nielsen et al., "Facile Synthesis of Reagents Containing a Terminal Maleimido Ligand Linked to an Active Ester," *Synthesis,* (1991), pp. 819–821.

Walker, "A High Yielding Synthesis of N–Alkyl Maleimides Using a Novel Modification of the Mitsunobu Reaction," *J. Org. Chem.,* (1995), vol. 60, pp. 5352–5355.

Reddy et al., "Lewis Acid and Hexamethyldisilazane–Promoted Efficient Synthesis of N–Alkyl–and N–Arylimide Derivatives," *The Journal of Organic Chemistry,* vol. 62, No. 8, pp. 2652–2654.

Simionescu et al., "Synthesis and Polymerization of N–(1–Anthryl)Maleimide," *Journal of Polymer Science,* (1990), vol. 28, pp. 39–45.

*Primary Examiner*—Floyd D. Higel
*Attorney, Agent, or Firm*—Burns, Doane, Swecker & Mathis, LLP

[57] ABSTRACT

Provided are methods for the synthesis of N-cyclic maleamic acids and N-cyclic maleimide derivatives, as well as N-cyclic maleamic acids and N-cyclic maleimides synthesized thereby. The method for synthesis of an N-cyclic maleamic acid involves reacting an amino group-containing N-cyclic compound with maleic anhydride in acetic acid to obtain an N-cyclic maleamic acid. An N-cyclic maleimide can be formed by adding hexamethyldisilazane to an N-cyclic maleamic acid prepared according to the above-described method, thereby cyclizing a maleamic acid site of the N-cyclic maleamic acid. The described methods allow for the products to be obtained at high yields.

7 Claims, 7 Drawing Sheets

EFFICIENT METHOD FOR THE SYNTHESIS OF N-CYCLIC MALEAMIC ACIDS AND N-CYCLIC MALEIMIDES

CROSS-REFERENCE TO RELATED APPLICATIONS

This application claims the benefit of priority under 35 U.S.C. §119 of Japanese Application No. 09(1997)-160454, the entire contents of which are incorporated herein by reference.

BACKGROUND OF THE INVENTION

1. Field of the Invention

The present invention relates to novel methods for the synthesis of N-cyclic maleimide acids and N-cyclic maleimide derivatives, and to novel N-cyclic maleimide acids and N-cyclic maleimide derivatives formed thereby.

2. Description of the Related Art

There are many known N-cyclic maleimide derivatives which are fluorescent substances. At present, such materials are widely used for the detection of nucleic acids, proteins, etc. In addition, these N-cyclic maleimides have many applications, such as use as monomers for raw materials in the chemical process industry. There is, therefore, an increasing demand for N-cyclic maleimide compounds.

Various techniques for the synthesis of maleimide derivatives have heretofore been proposed, all of which, however, result in low yields of maleimide derivatives.

Among the conventional methods for the synthesis of maleimide derivatives, a first method comprises reacting maleic anhydride with amines in ether to obtain a nearly quantitative yield of the corresponding N-substituted maleimide acid. Then, acetic anhydride and sodium acetate are added to the resulting maleamic acid, followed by heating at 100° C. for dehydration to obtain the corresponding maleimide derivatives at a yield of 50 to 70% (see Mehta et al., J. Org. Chem., 1960, 25, 1012).

A second method comprises reacting maleic anhydride with an appropriate amino compound in ether to obtain a nearly quantitative yield of the corresponding maleamic acid. This is followed by heating under reflux in a mixture of triethylamine and toluene for dehydration of the maleamic acid to obtain the corresponding maleimide at a yield of 20% (see Meyers et al., J. Org. Chem., 1989, 54, 4243).

A third method comprises reacting maleic anhydride with an appropriate amino compound in ether to obtain a nearly quantitative yield of the corresponding maleamic acid, and then adding thereto a carbodiimide to obtain an isoimide. This is followed by heating the resulting isoimide in a mixture of hydroxybenzotriazole and toluene for 18 hours at 100° C., to obtain the corresponding maleimide at a yield of 47% (see Garner et al., J. Org. Chem., 1991, 55, 5893).

A fourth method comprises reacting maleic anhydride with an amino compound in ether to obtain a nearly quantitative yield of the corresponding maleamic acid. This is then reacted with dicyclohexylcarbodiimide in a solvent of acetic acid and dimethylformamide for dehydration of the maleamic acid to obtain the corresponding maleimide at a yield of 75% (see Nielsen et al., Synthesis, 1991, 819).

The above-described methods are, however, not suitable for the synthesis of aliphatic maleimide derivatives. Furthermore, these methods result in N-cyclic maleimides of low yield.

A fifth method comprises reacting a maleimide with an aliphatic alcohol in a mixture of diisopropyl azodicarboxylate and acetic acid at room temperature for 18 hours. The corresponding aliphatic maleimide derivatives are obtained at a yield of from 83 to 92% (see Walker, J. Org. Chem., 1995, 60, 5352). This method is suitable for the synthesis of aliphatic maleimides, but could not be used for synthesizing N-aromatic maleimides.

A sixth method comprises an acid catalyzed dehydration of an amine and anhydride at reflux temperature. This results in the corresponding maleimide at a yield of 82% (see Yuichi Kita et al., Report in the 72nd Spring Meeting of the Chemical Society of Japan). The yield for this method is low. In addition, fluorescent aromatic maleimide derivatives synthesized according to this method provide low yields.

A seventh method comprises reacting maleic anhydride with an amine in benzene at room temperature, and then adding thereto hexamethyldisilazane, and zinc bromide or zinc chloride. This is followed by heating under reflux in benzene to obtain an aliphatic or benzyl-type maleimide at a yield of from 73 to 98% (see P. Y. Reddy, Toru et al., J. Org. Chem. in press). When fluorescent aromatic maleimides are synthesized according to this method, the starting compounds used remain in the reaction mixture without being reacted completely. This results in a low yield of maleimide derivatives.

As mentioned above, the conventional methods for synthesis of N-cyclic maleimide derivatives are all problematic, and the yields associated therewith are low. In addition, some types of N-cyclic maleimides are difficult to produce thereby.

SUMMARY OF THE INVENTION

In consideration of the problems associated with the related art, the present invention provides a method for synthesizing N-cyclic maleamic acids and a method for synthesizing N-cyclic maleimides, in which methods the products can be formed at high yields. In addition, novel N-cyclic maleamic acids and N-cyclic maleimide derivatives are provided by the methods.

According to a first aspect of the invention, a novel method for synthesis of an N-cyclic maleamic acid is provided. The method comprises reacting an amino group-containing N-cyclic compound with maleic anhydride in acetic acid to obtain an N-cyclic maleamic acid.

According to a second aspect of the invention, an N-cyclic maleamic acid is provided. The N-cyclic maleamic acid comprises an amino group-containing N-cyclic structure and maleic anhydride bonded together via a maleamic bond.

According to a third aspect of the invention, provided is a method for synthesis of an N-cyclic maleimide. The method comprises adding hexamethyldisilazane to an N-cyclic maleamic acid prepared according to the above-described method, thereby cyclizing a maleamic acid site of the N-cyclic maleamic acid to provide an N-cyclic maleimide.

According to a fourth aspect of the invention, an N-cyclic maleimide is provided. The maleimide is synthesized by cyclizing an N-cyclic maleamic acid at the maleamic acid site thereof.

The methods in accordance with the invention allows for the products to be obtained at high yields.

DETAILED DESCRIPTION OF THE PREFERRED EMBODIMENTS OF THE INVENTION

Figure 1:
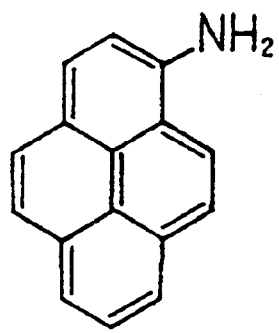
FIG. 1 illustrates the chemical structural formula of 1-aminopyrene, which can be used in accordance with a method of the invention.

In accordance with one aspect of the invention, a method for the synthesis of N-cyclic maleamic acids is provided. The method comprises reacting an amino group-containing N-cyclic substituent with maleic anhydride in acetic acid to obtain the corresponding N-cyclic maleamic acid.

A characteristic feature of the invention is the use of acetic acid in the reaction of the N-cyclic amine with the maleic anhydride. In acetic acid, N-cyclic amines are efficiently reacted with maleic anhydride to give an N-cyclic maleamic acid at high yield. Therefore, many types of N-cyclic maleamic acids can be synthesized in accordance with this aspect of the invention.

The N-cyclic maleamic acid obtained from reaction of the N-cyclic amine and maleic anhydride is preferably washed with ether. This washing results in the removal of excess, unreacted amine from the N-cyclic maleamic acid. In order to improve the efficiency of the N-cyclic maleamic acid product washing, an organic solvent such as ether, ethyl acetate, methylene chloride, etc., is preferably used.

The amount of maleic anhydride to be reacted is preferably from 1 to 1.2 mol equivalents relative to one mol equivalent of the N-cyclic compound. Within the defined range, the starting compounds (i.e., the N-cyclic compound and the maleic anhydride) are reacted more efficiently to give a higher yield of the product (i.e., N-cyclic maleamic acid).

If, however, the amount of maleic anhydride is smaller than 1 mol equivalent relative to one mol equivalent of the N-cyclic acid, or is larger than 1.2 mol equivalents, the excess maleic anhydride or N-cyclic compound will remain unreacted in the reaction system. This often lowers the yield of the N-cyclic maleamic acid product.

The N-cyclic amine is constructed such that a plurality of rings, of which the cyclic skeleton consists essentially of carbon atoms, are condensed together. It can include, for example, carbocyclic compounds in which the cyclic skeleton includes carbon atoms only, and heterocyclic compounds in which the cyclic skeleton includes carbon atoms and hetero atoms, such as oxygen, nitrogen and/or sulfur atoms. The cyclic skeleton may be, for example, a 5-membered or 6-membered ring or the like, and may include saturated bonds only or a combination of saturated and unsaturated bonds. For example, the N-cyclic compound preferably has an N-cyclic structure of any of the fluorophore groups. Compound of this type can provide the object N-cyclic maleamic acids at high yield.

The N-cyclic compound has an amino group which may be bonded to any position of the cyclic structure of the compound.

The temperature at which the N-cyclic amine compound is reacted with the maleic anhydride in acetic acid is preferably between −10 and 100° C. Within that temperature range, the two can react efficiently to give a higher yield of the N-cyclic maleamic acid product.

According to yet another aspect of the invention, provided are novel N-cyclic maleamic acids each composed of an amine group-containing N-cyclic substituent and maleic anhydride as bonded together via a maleamic bond.

The N-cyclic maleamic acids can be synthesized in the method noted above at high yield. Many of these novel substances, obtained according to the method noted above, emit fluorescence when exposed to light. Therefore, they are expected to be widely usable in various fields of chemistry and biochemistry as fluorescent and chemiluminescent substances. The N-cyclic maleamic acids include, for example, those having an N-cyclic structure of any of the fluorophore groups.

The N-cyclic maleamic acids in accordance with the invention are constructed such that the ring-cleaved structure of maleic anhydride (—CO—CH=CH—COOH) is bonded to the amino group ($NH_2$) of the starting N-cyclic amine compound via an maleamic bond (—NH—CO—) therebetween. In the N-cyclic maleamic acids, the maleamic bonding site may be at any position of the cyclic structure. For example, the N-cyclic maleamic acids may have one or more substituent bonded to the carbon-N-cyclic moiety. In this regard, the substituent(s) may be bonded to any one or more positions of the carbon-N-cyclic moiety.

The substituents may be one or more selected from the group consisting of a halogen atom, a hydroxyl group, an alkyl group, an amino group and a thiol group.

The N-cyclic maleamic acids having such substituent(s) may also be synthesized according to the method noted above at high yield.

The method for synthesizing N-cyclic maleimide derivatives in accordance with the invention will now be described. The method comprises adding hexamethyldisilazane (HMDS) to the N-cyclic maleamic acid obtained according to the above-described method. The maleamic acid site of the N-cyclic maleamic acid is cyclized to give an N-cyclic maleimide derivative. A characteristic feature of this method of the invention is in starting from the N-cyclic maleamic acid obtained according to the above-described method, as well as in the cyclization.

In accordance with the invention, since the N-cyclic maleamic acids obtained at high yields in the manner mentioned above are used as starting compounds, the yield of the N-cyclic maleimide product is likewise high.

In the synthesis of N-cyclic maleimides, where HMDS is added to the N-cyclic maleamic acid, the maleamic acid is dehydrated at the position between the terminal group (—COOH) of the maleamic acid and the secondary amine (—NH—) of the maleamic bond of the acid. The carbonyl group of the terminal group is thereby connected with the nitrogen atom of the secondary amino to form a cyclic structure. As a result of this cyclization, a maleimide of an N-cyclic substituted amine, that is, an N-cyclic substituted maleimide, is obtained.

The cyclization is preferably effected in benzene or a benzene/dimethyl formamide (DMF) mixture. In this mode, the dehydration is promoted more efficiently to give the intended N-cyclic maleimide at higher yield.

A Lewis acid can be added to promote the cyclization reaction. In this mode, the cyclized compound, N-cyclic maleimide, can be obtained at high yield.

The Lewis acid is preferably one or more selected from the group consisting of zinc halides, aluminium halides, tin halides, titanium halides, magnesium halides, trifluoroborane-etherate complexes and combinations thereof. Using a Lewis acid of this type, the yield of the cyclized compound, N-cyclic maleimide, is increased considerably.

The zinc halides include, for example, $ZnCl_2$, $ZnBr_2$, $ZnI_2$, etc., while the metal halides include, for example, fluorides, chlorides, bromides, iodides, etc.

The cyclization is preferably effected at a temperature between 50 and 250° C. Within the defined temperature range, the production of side products can be inhibited. If the temperature is lower than 0° C. the dehydration will be retarded.

The cyclization is preferably effected under heat for reflux. In this mode, the reaction efficiency is increased, such that the object N-cyclic maleimides can be obtained at higher yields.

The N-cyclic maleimide derivatives obtained through cyclization of the maleamic acid moiety of an N-cyclic maleamic acid will now be discussed. The N-cyclic maleimides produced according to the above-described method can be obtained at high yield. These N-cyclic maleimides produced by the above method are novel substances which will emit fluorescence when exposed to light. Therefore, they are expected to be widely usable in various fields of chemistry and biochemistry as fluorescent and chemiluminescent substances.

The N-cyclic maleimides may have an N-cyclic structure of any of the fluorophore groups. For example, the N-cyclic maleimides may have one or more substituents bonded to the carbon-N-cyclic moiety. The substituent(s) may be bonded to any one or more positions of the carbon-N-cyclic moiety.

The substituents may, for example, be one or more selected from the group consisting of a halogen atom, a hydroxyl group, an alkyl group, an amino group and a thiol group. The N-cyclic maleimides having such substituent(s) may also be synthesized according to the method noted above at a high yield.

Many of the N-cyclic maleimides of the invention emit fluorescence. Therefore, where any of the compounds are, as a labeling compound, bonded to a sample to be tested, the sample can be detected. For example, as samples to be tested, nucleic acids, proteins, minor components in organisms and other materials can be detected at high sensitivity. In addition, since the N-cyclic maleimides of the invention are useful raw materials for chemical products, they have many other applications in various fields.

The invention will now be described in more detail with reference to the following examples which, however, are not intended to restrict the scope of the invention.

EXAMPLE 1

Figure 16:
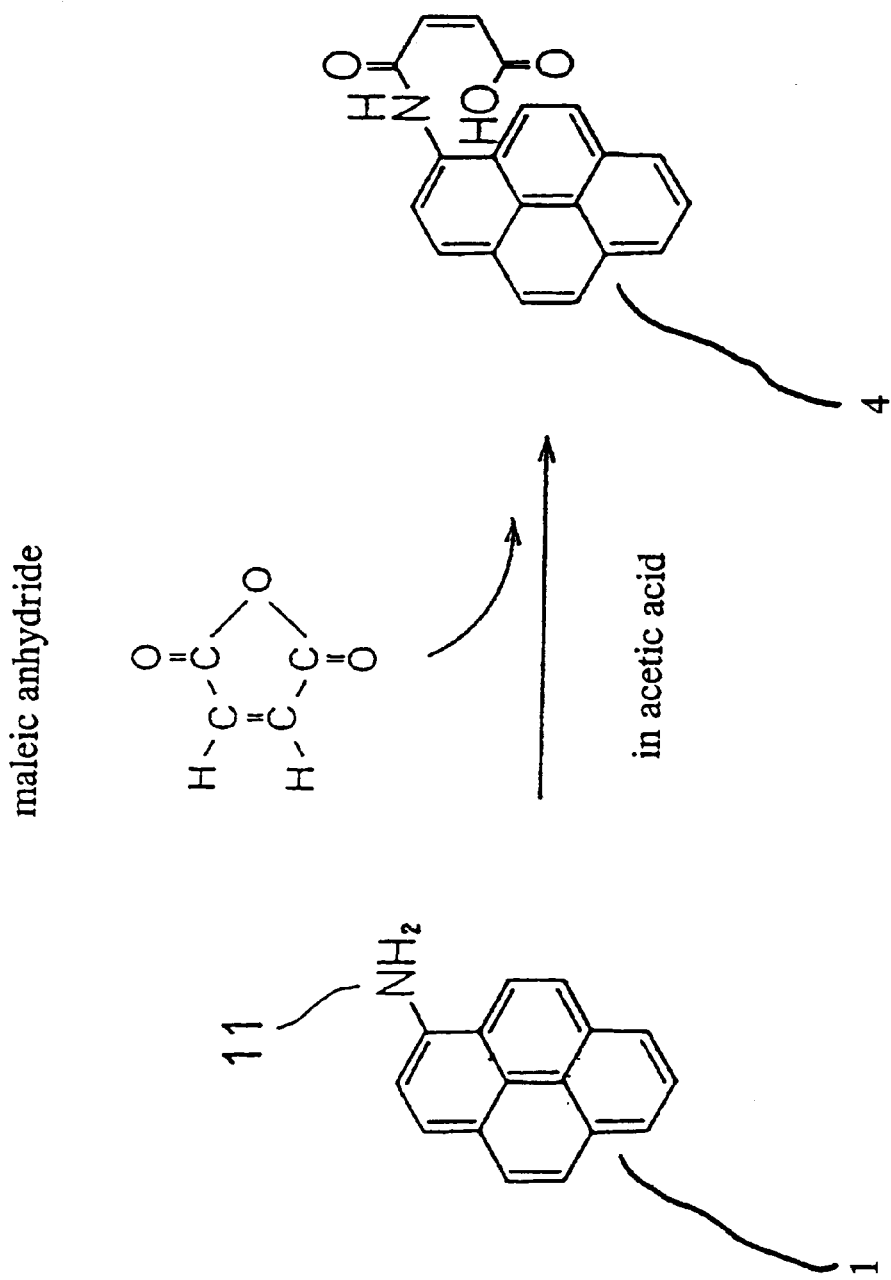
FIG. 16 illustrates the reaction of 1-aminopyrene and maleic anhydride in Example 1.
Figure 17:
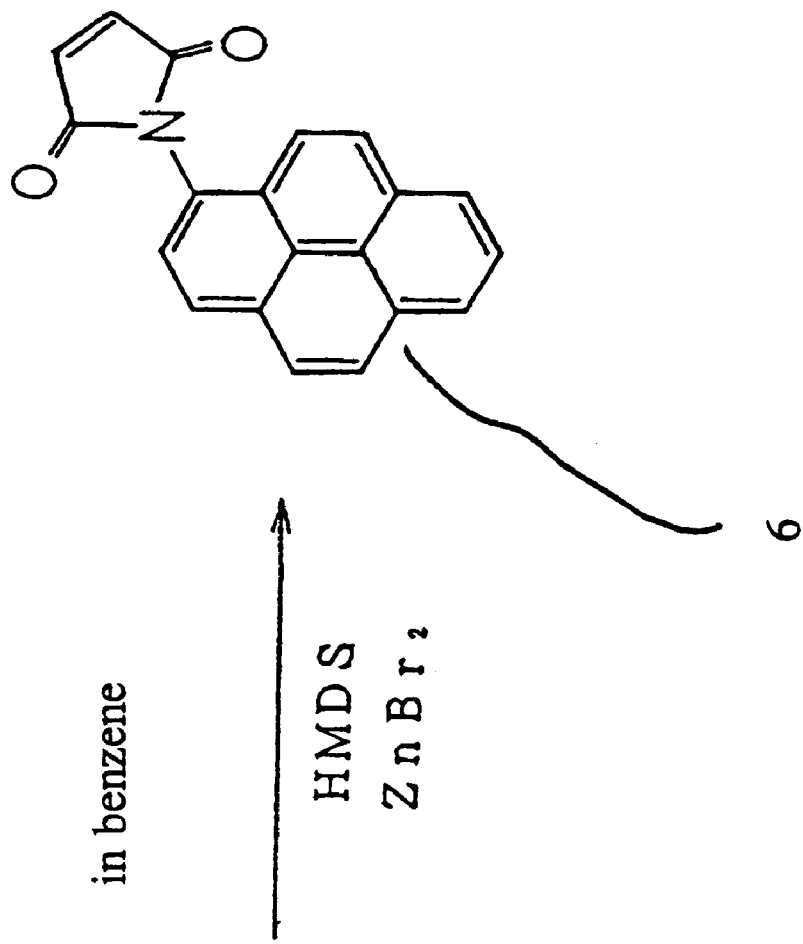
FIG. 17 illustrates the cyclization of 1-pyrenemaleamic acid in Example 1.
Figure 17:
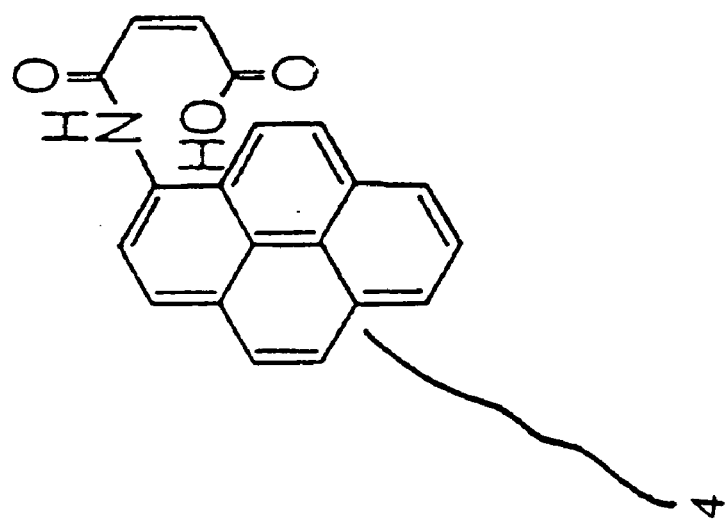

With reference to FIG. 1, FIG. 6, FIG. 11, FIG. 16 and FIG. 17, this example demonstrates the synthesis of N-cyclic maleimides in accordance with the invention, Referring to FIG. 16, an N-cyclic compound 1 having an amino group 11 is reacted with maleic anhydride in acetic acid to give an N-cyclic maleamic acid 4. With reference to FIG. 17, HMDS and a Lewis acid ($ZnBr_2$) are next added to the N-cyclic maleamic acid 4 in benzene, to thereby cyclize the maleamic acid moiety of the acid 4 to give an N-cyclic maleimide 6.

The method for synthesis of the N-cyclic maleimide will now be described in detail. First, 0.505 mmols of an N-cyclic compound of 1-aminopyrene (FIG. 1) was reacted with 1.1 mol equivalents of maleic anhydride in 5 ml of acetic acid at room temperature for 17 hours. After the reaction, a precipitate of yellow crystals was obtained. The precipitate was removed through suction filtration and washed with ethyl acetate. An N-cyclic maleamic acid of 1-pyrenemaleamic acid (FIG. 6) was obtained at a yield of 95%.

Next, 1 mol equivalent of zinc bromide ($ZnBr_2$) and 1.5 mol equivalents of HMDS were added to 0.227 nunols of the 1-pyrenemaleamic acid, and heated under reflux in benzene for 30 minutes. After the reaction, the solvent, benzene, was removed, and the residue was extracted with ethyl acetate. The resulting extract was purified through column chromatography (hexane/ethyl acetate=8/2). The product, 1-pyrenemaleimide (FIG. 11), was thereby obtained at a yield of 98%.

EXAMPLE 2

Figure 2:
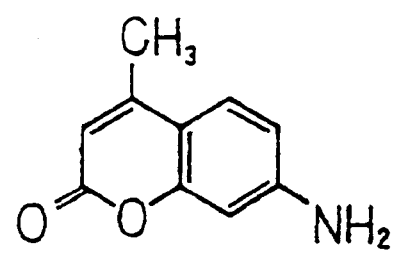
FIG. 2 illustrates the chemical structural formula of 7-amino-4-methylcoumarin, which can be used in accordance with a method of the invention.
Figure 7:
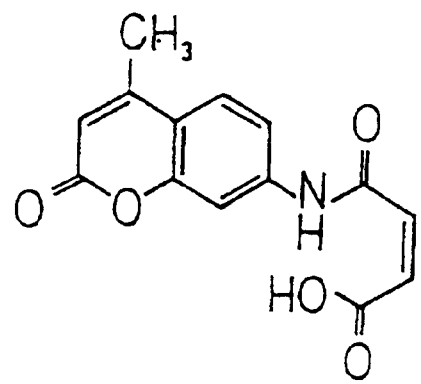
FIG. 7 illustrates the chemical structural formula of (4-methylcoumarin)-7-maleamic acid, prepared in accordance with the invention.
Figure 12:
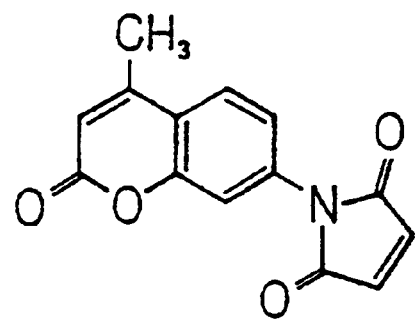
FIG. 12 illustrates the chemical structural formula of (4-methylcoumarin)-7-maleimide, prepared in accordance with the invention.

In this example, starting from 7-amino-4-methylcoumarin (FIG. 2), (4-methylcoumarin)-7-maleamic acid (FIG. 7) was produced. From this, 4-methylcoumarin-7-maleimide (FIG. 12) was obtained.

1.044 mmols of 7-amino-4-methylcoumarin was first reacted with 1.1 mol equivalents of maleic anhydride in 15 ml of acetic acid at room temperature for 36 hours. After the reaction, a precipitate of yellow crystals was obtained. The precipitate was removed through suction filtration and washed with ether. (4-methylcoumarin)-7-maleamic acid was obtained at a yield of 87%.

Next, 1 mol equivalent of zinc bromide and 1.5 mol equivalents of HMDS were added to 0.136 mmols of (4-methylcoumarin)-7-maleamic acid, and heated under reflux in a benzene/DMF (1:1) mixture for 1.5 hours. After the reaction, the solvent, benzene, was removed, and the residue was extracted with chloroform. The resulting extract was purified through column chromatography (hexane/ethyl acetate =8/2). (4-methylcoumarin)-7-maleimide was obtained at a yield of 97%.

EXAMPLE 3

Figure 3:
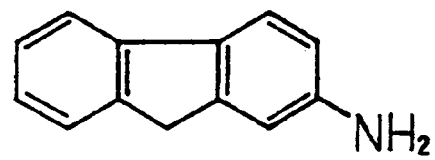
FIG. 3 illustrates the chemical structural formula of 7-aminofluorene, which can be used in accordance with a method of the invention.
Figure 8:
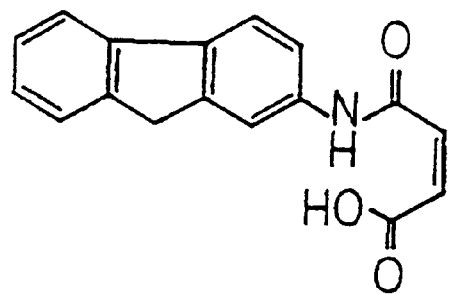
FIG. 8 illustrates the chemical structural formula of 2-fluorenmaleamic acid, prepared in accordance with the invention.
Figure 13:
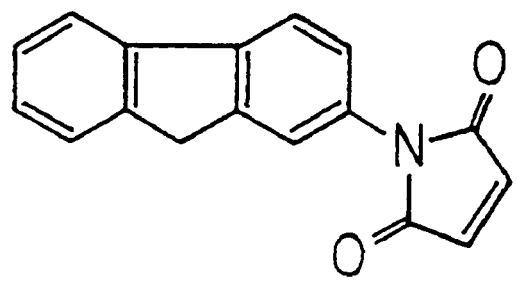
FIG. 13 illustrates the chemical structural formula of 2-fluorenemaleimide, prepared in accordance with the invention.

In this example, starting from 2-aminofluorene (FIG. 3), 2-fluorenmaleamic acid (FIG. 8) was produced. From this, 2-fluorenemaleimide (FIG. 13) was obtained.

3.311 mmols of 2-aminofluorene was first reacted with 1 mol equivalent of maleic anhydride in 30 ml of acetic acid at room temperature for 1.5 hours. After the reaction, a precipitate of yellow crystals was obtained. The precipitate was removed through suction filtration and washed with ether. 2-fluoremaleamic acid was thereby obtained at a yield of 94%.

Next, 1 mol equivalent of zinc bromide and 1.5 mol equivalents of HMDS were added to 0.451 mmols of 2-fluorenmaleamic acid, and heated under reflux in a benzene/DMF (1:1) mixture for 1.5 hours. After the reaction, the solvent, benzene, was removed, and the residue was extracted with ethyl acetate. The resulting extract was purified through column chromatography (hexane/ethyl acetate=8/2). 2-fluorenemaleimide was obtained at a yield of 93%.

EXAMPLE 4

Figure 4:
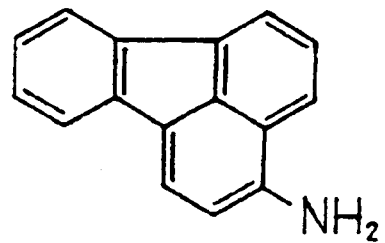
FIG. 4 illustrates the chemical structural formula of 3-aminofluoranthene, which can be used in accordance with a method of the invention.
Figure 9:
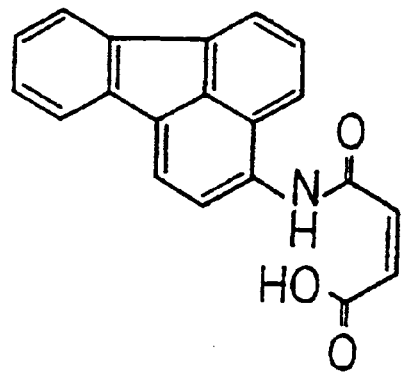
FIG. 9 illustrates the chemical structural formula of 7-fluoranthenmaleamic acid, prepared in accordance with the invention.
Figure 14:
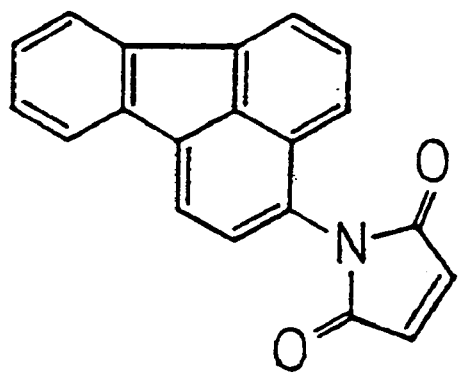
FIG. 14 illustrates the chemical structural formula of 3-fluoranthenemaleimide, prepared in accordance with the invention.

In this example, starting from 3-aminofluoranthene (FIG. 4), 3-fluoranthenmaleamic acid (FIG. 9) was produced. From this, 3-fluoranthenemaleimide (FIG. 14) was obtained.

3.222 mmols of 3-aminofluoranthene was first reacted with 1 mol equivalent of maleic anhydride in 30 ml of acetic acid at room temperature for 3 hours. After the reaction, a precipitate of yellow crystals was obtained. The precipitate was then removed through suction filtration, and washed with ether. 3-fluoranthenmaleamic acid was obtained at a yield of 92%.

Next, 1 mol equivalent of zinc bromide and 1.5 mol equivalents of HMDS were added to 0.415 mmols of 3-fluoranthenmaleamic acid, and heated under reflux in benzene for 4 hours. After the reaction, the solvent, benzene, was removed, and the residue was extracted with ethyl acetate. The resulting extract was purified through column chromatography (hexane/ethyl acetate=8/2). 3-fluoranthenemaleimide was obtained at a yield of 93%.

EXAMPLE 5

Figure 5:
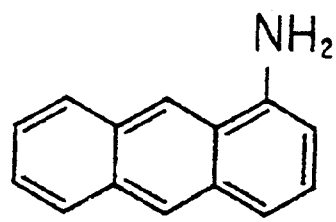
FIG. 5 illustrates the chemical structural formula of 1-aninoanthracene, which can be used in accordance with a method of the invention.
Figure 6:
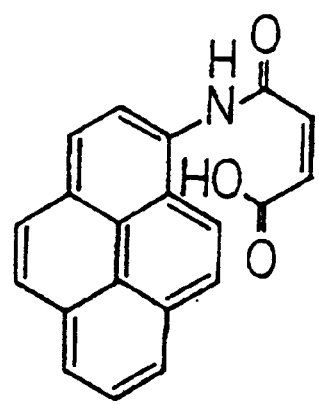
FIG. 6 illustrates the chemical structural formula of 1-pyrenemaleamic acid, prepared in accordance with the invention.
Figure 10:
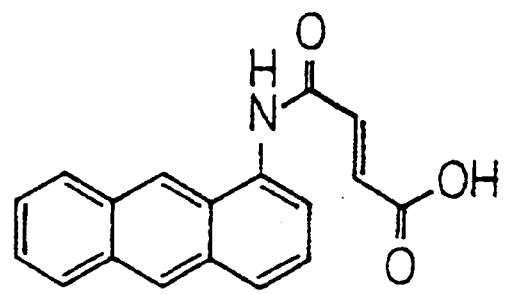
FIG. 10 illustrates the chemical structural formula of 1-anthracenmaleamic acid, prepared in accordance with the invention.
Figure 11:
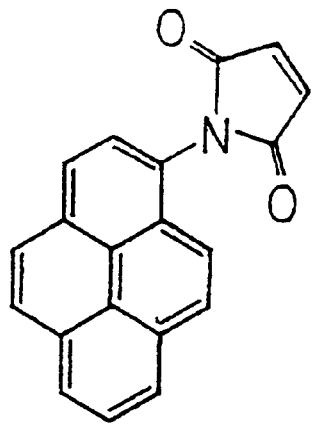
FIG. 11 illustrates the chemical structural formula of 1-pyrenemaleimide, prepared in accordance with the invention.
Figure 15:
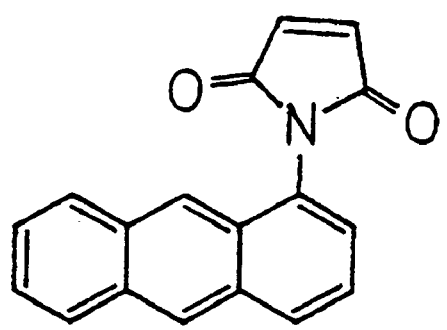
FIG. 15 illustrates the chemical structural formula of 1-anthracenemaleimide, prepared in accordance with the invention.

In this example, starting from 1-aminoanthracene (FIG. 5), 1-anthracenmaleamic acid (FIG. 10) was produced. From this, 1-anthracenemaleimide (FIG. 15) was obtained.

0.531 mmols of 1-aminoanthracene was first reacted with 1.1 mol equivalents of maleic anhydride in 10 ml of acetic acid at room temperature for 4 hours. After the reaction, a precipitate of yellow crystals was obtained. The precipitate was then removed through suction filtration, and washed with ether. 1-anthracenmaleamic acid was obtained at a yield of 78%.

Next, 1.5 mol equivalents of zinc chloride and 1.5 mol equivalents of HMDS were added to 0.0892 mmols of anthracenmaleamic acid, and heated under reflux in benzene for 1.5 hours. After the reaction, the solvent, benzene, was removed, and the residue was extracted with ethyl acetate. The resulting extract was purified through column chromatography (hexane/ethyl acetate=8/2). 1-anthracenemaleimide was obtained at a yield of 93%.

The structures of the N-cyclic maleamic acids and the N-cyclic maleimides synthesized in Examples 1 to 5 were identified through NMR, IR and mass spectrometry and elementary analysis.

The reaction conditions employed in Examples 1 to 5 and the yields of the products obtained therein are shown in Tables 1 and 2. In particular, Table 1 shows the reaction conditions for synthesizing the N-cyclic maleamic acid illustrated in FIG. 16, the yield of the product and the starting compound used. Table 2 shows the reaction conditions for synthesis of the N-cyclic maleimide illustrated in FIG. 17, the yield of the product and the starting compound used.

TABLE 1

| | Polycyclic Compound | | Reaction Conditions | | | |
|---|---|---|---|---|---|---|
| Example | (starting substance) | Polycyclic Amido Acid (product) | Solvent | Temperature | Time | Yield |
| 1 | 1-Aminopyrene | 1-Pyrenamido Acid | AcOH | room temperature | 17 hrs | 95% |
| 2 | 7-Amino-4-methylcoumarin | (4-Methylcoumarin)-7-amido Acid | AcOH | room temperature | 36 hrs | 87% |
| 3 | 2-aminofluorene | 2-Fluorenamido Acid | AcOH | room temperature | 1.5 hrs | 94% |
| 4 | 3-Aminofluoranthene | 3-Fluorancenamido Acid | AcOH | room temperature | 3 hrs | 92% |
| 5 | 1-Aminoanthracene | 1-Anthracenamido Acid | AcOH | room temperature | 4 hrs | 78% |

TABLE 2

| Example | Polycyclic Amido Acid (starting substance) | Polycyclic Maleimide (product) | Reaction Conditions | | |
|---|---|---|---|---|---|
| | | | Lewis Acid | Time | Yield |
| 1 | 1-Pyrenamido Acid | 1-Pyrenemaleimide | $ZnBr_2$ | 0.5 hrs | 98% |
| 2 | (4-Methylcoumarin)-7-amido Acid | (4-Methylcoumarin)-7-maleimide | $ZnBr_2$ | 1.5 hrs | 97% |
| 3 | 2-Fluorenamido Acid | 2-Fluorenemaleimide | $ZnBr_2$ | 1.5 hrs | 93% |
| 4 | 3-Fluorancenamido Acid | 3-Fluorancenemaleimide | $ZnB_2$ | 4 hrs | 93% |
| 5 | 1-Anthracenamido Acid | 1-Anthracenemaleimide | $ZnCl_2$ | 1.5 hrs | 90% |

As described in detail hereinabove, the present invention provides methods for the synthesis of N-cyclic maleamic acids and methods for the synthesis N-cyclic maleimide derivatives, in which the products are obtained in high yield. In addition, the methods provide novel N-cyclic maleamic acids and N-cyclic maleimides.

While the invention has been described in detail with reference to specific embodiments thereof, it will be apparent to one skilled in the art that various changes and modifications can be made therein without departing from the spirit and scope thereof.

What is claimed is:

1. A method for synthesis of an N-cyclic maleimide, comprising adding hexamethyldisilazane to an N-cyclic maleamic acid, the N-cyclic maleamic acid being prepared by a method comprising reacting an amino group-containing N-cyclic compound with maleic anhydride in acetic acid, thereby cyclizing a maleamic acid site of said N-cyclic maleamic acid to provide an N-cyclic maleimide.

2. The method according to claim 1, wherein the cyclizing is effected in benzene or in a benzene/dimethyl formamide mixture.

3. The method according to claim 1, wherein the cyclizing is effected in a 1:1 benzene/dimethyl formamide mixture.

4. The method according to claim 1, further comprising adding a Lewis acid for the cyclizing.

5. The method according to claim 4, wherein said Lewis acid is selected from the group consisting of zinc halides, aluminium halides, tin halides, titanium halides, magnesium halides, a trifluoroborane-etherate complex, or combinations thereof.

6. The method according to claim 1, wherein said cyclizing is effected at a temperature of between 50 and 250° C.

7. The method according to claim 1, wherein said cyclizing is effected under heat for reflux.

* * * * *